United States Patent [19]
Ghelli

[11] 4,217,457
[45] Aug. 12, 1980

[54] HIGHLY SELECTIVE OXIDIZING PROCESS FOR PREPARING PYRIDIN-CARBOXYLIC ACIDS

[75] Inventor: Giovanni Ghelli, Savona, Italy

[73] Assignee: Luigi Stoppani S.p.A., Milan, Italy

[21] Appl. No.: 924,619

[22] Filed: Jul. 14, 1978

[30] Foreign Application Priority Data

Jul. 18, 1977 [IT] Italy ............................... 25812 A/77

[51] Int. Cl.$^2$ ...................... C07B 3/00; C07D 213/79; C07D 213/80
[52] U.S. Cl. .................................. 546/320; 546/318; 546/327
[58] Field of Search ....................... 546/318, 320, 327

[56] References Cited

U.S. PATENT DOCUMENTS

| 2,415,147 | 2/1947 | Ogilvie et al. | 546/320 |
| 3,154,549 | 10/1964 | Beck | 546/320 X |
| 3,313,821 | 4/1967 | Lekberg et al. | 546/320 |

Primary Examiner—Richard Raymond
Attorney, Agent, or Firm—Fleit & Jacobson

[57] ABSTRACT

A highly selective oxidation process for preparing pyridin-carboxylic acids from pyridine compounds nucleus substituted with alkyl groups, through a carbon-carbon bond, and oxidizable to carboxyl, and from hydrosoluble hexavalent chromium compounds, in the presence of an acid.

Particularly described is the oxidation of beta-picoline with sodium bichromate to obtain the sodium salt of nicotinic acid and 99.5% pure free acid, respectively.

16 Claims, No Drawings

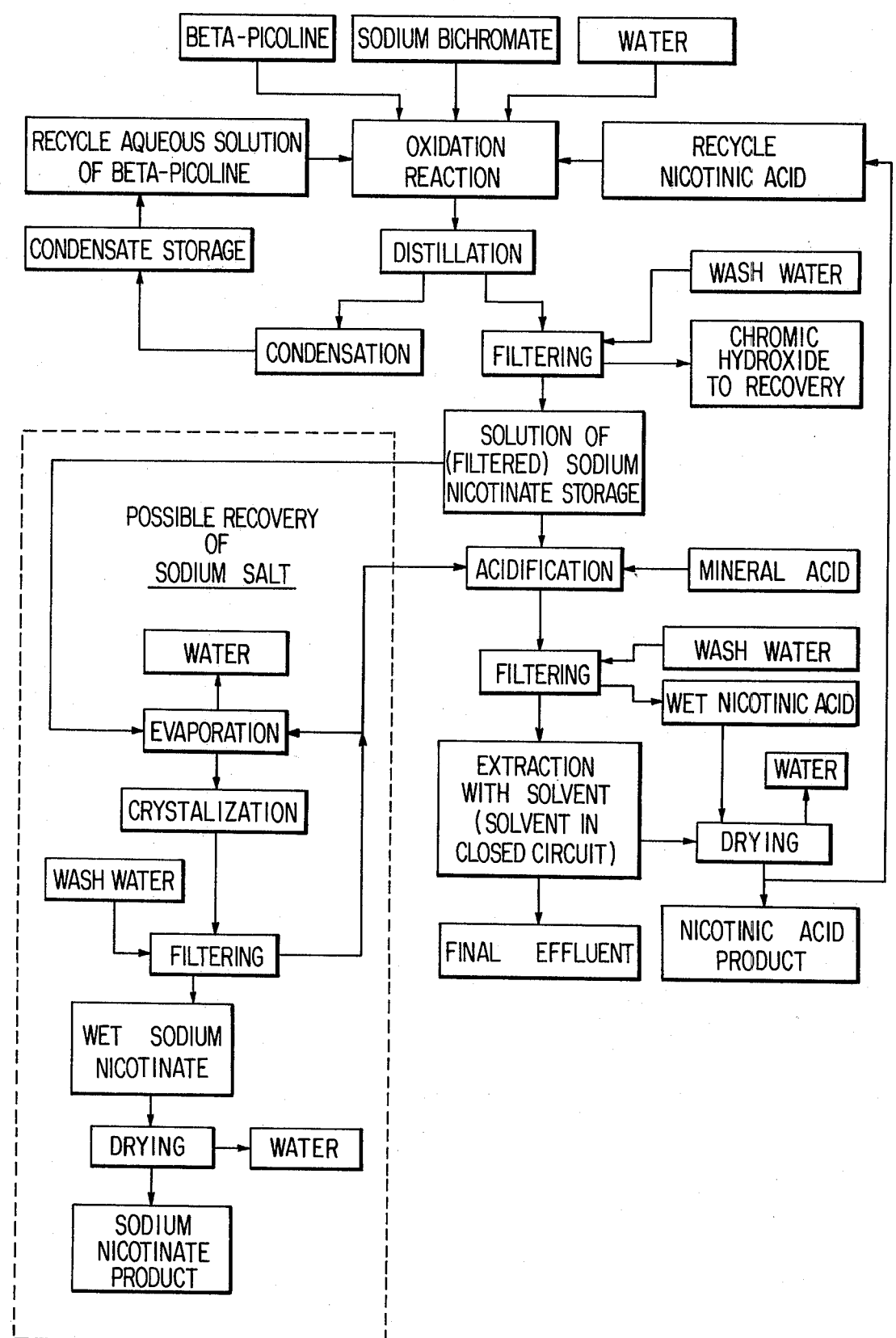

HIGHLY SELECTIVE OXIDIZING PROCESS FOR PREPARING PYRIDIN-CARBOXYLIC ACIDS

This invention relates to a highly selective oxidizing process for preparing pyridin-carboxylic acids. Particularly, the oxidation is carried out on alkyl organic groups attached to a pyridine nucleus by carbon-carbon bonds and liable to oxidation to carboxylic groups. Under the specific conditions, as disclosed and claimed in the following, such an oxidation is carried out with water-soluble, hexavalent chromium salts.

More particularly, the present invention refers to oxidizing beta-picoline with sodium bichromate to provide nicotinic acid and its sodium salt, which is a product of significant commercial interest.

Processes for oxidizing pyridine compounds according to the above outlined general scheme are already known.

Such processes are particularly disclosed in U.S. Pat. No. 2,415,147 and U.S. Pat. No. 3,313,821.

In its primary claim, said U.S. Pat. No. 2,415,147 discloses the oxidation of heterocyclic compounds containing in the structure thereof a pyridine nucleus, substituted by organic groups, attached to said nucleus by one or more carbon to carbon bonds and oxidizable to carboxylic acid. This oxidation is carried out by means of neutral or alkaline aqueous solutions in the form of the soluble metal salt, for example sodium salt, being recovered therefrom in a per se known manner by acidification of carboxylic acid and nicotinic acid, respectively. The reaction is carried out in an environment with a pH close to 7 and at a temperature of at least 150° C., in the presence of a pressure equivalent to the vapor pressure of the reactive mixture at the indicated temperature.

Unlike the above described process (U.S. Pat. No. 3,313,821), the process according to the present invention does not use the step of altering the starting compound having the pyridine nucleus carrying a substituent oxidizable to carboxylic acid and, by oxidizing with water-soluble, hexavalent chromium salts. Under specific conditions, hereinafter discussed and claimed, important advantages over the process of said U.S. Pat. No. 3,313,821 are attained.

Such advantages can be essentially summarized as follows:

(1) High value of selectivity and yield, which is substantially around 100%, this being of significant interest in an industrial process.

(2) Possibility of certainly achieving complete reduction and insolubilization of the oxidant, formed of a water-soluble hexavalent chromium compound, in the form of trivalent chromium hydroxide as a result of using oxidant proportions in a lower amount than the equivalent stoichiometrical value required by the pyridine compound reacting therewith. Thus, the complicated removal of the unreacted oxidant is avoided, insuring the total absence of toxicity in the final product, which may have an essential significance for certain uses of the latter.

(3) Reduction in processing times relative to those indicated in the above mentioned patents, since the reaction according to the process of the present invention is carried out in a "homogeneous" phase. However, such times do not exceed 4 hours, if the temperature is maintained at at least 200° C., at the pressure occurring in the autoclave at the vapor pressure of the mixture reacting at that temperature.

(4) Possibility of using on a large scale less valuable and accordingly less expensive apparatus materials in that the reaction is carried out in the restricted range of pH between 4.5 and 8.5.

(5) Obtainment of an exceedingly pure final product, both in the form of alkaline salt and in the form of acid, from a substantially neutral final solution containing only the above alkaline salt of carboxylic acid.

The high yield, which is a further economic advantage, is derived partly from the carboxylic acid recovered in the final stage being recycled to the reaction phase, as well as the excess of pyridine compound.

Some theoretical considerations will now be disclosed in the following for explaining the development of the process according to the present invention. Starting from beta-picoline (3-methylpyridine $C_5H_4N(CH_3)$), for example, the same is treated with aqueous solution of sodium bichromate.

The reaction develops according to the following scheme:

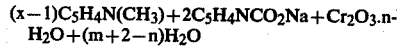

Namely an excess of beta-picoline is reacted in the presence of nicotinic acid, as acidificant, with an aqueous solution of sodium bichromate as oxidant, obtaining sodium nicotinate, an excess of beta-picoline in aqueous solution and insoluble chromic hydroxide. Substantially, under the disclosed operating conditions, index "n" is equal to 2, which means that the final amount of water corresponds to the initial amount of water.

The concentration of the aqueous solution of sodium bichromate should be such that the sodium nicotinate being formed is in solution at all of the process stages. This facilitates solid-liquid separation and prevents, at reaction temperature, the possible phenomena of salt decomposition, which salt may be in crystalized state, with the development of carbon dioxide and appearance of pyridine, with a resulting yield loss.

It was found that the desired conditions perfectly occur when the value of index "m" is not lower than 40. In such a case, the initial reaction mixture is present in the form of a homogeneous phase, provided that the value taken by x is at least 1.3. This because under these general conditions and with these molar ratios, the conditions as imposed by the solubility values of sodium bichromate in water and by the ternary diagram of mutual solubility between water, beta-picoline and nicotinic acid are met.

The foregoing disclosure for the particular case of nicotinic acid oxidation of beta-picoline is also true for the other substituted pyridines, among which are particularly gamma-picoline and methylethyl-pyridine.

Conveniently, the reaction temperature may be selected in the range of between 150°–300° C., depending on the selected reaction time and pyridine compound to be oxidized. However, the preferred range is between 175° C. and 250° C.

When maintaining the above disclosed conditions, the nicotinic acid cited as an example, being recycled as acidificant in the reaction, is surprisingly stable under the reaction conditions and is completely recovered along with that being generated by oxidation.

The process according to the present invention substantially consists of the following stages:

(A) reaction in homogeneous phase carried out in an autoclave in aqueous solution, between a pyridine derivative and sodium bichromate, the latter being present in a lower amount than the stoichiometrical amount required by the pyridine derivative, in the presence of nicotinic acid in the same amount as that which will be formed by reaction at a temperature between 150° and 300° C. (preferably between 175° and 250° C.), at pH between 4.5 and 8.5 (preferably between 5.5 and 8.0) and at a pressure corresponding to the vapor pressure of the mixture reacting at such a temperature, for the time as required for the complete reduction of hexavalent chromium which is between about 1 and 8 hours;

(B) partial distillation of the slurry discharged from the autoclave, so as to separate the same in an aqueous condensate, of a nearly unitary specific gravity, containing the excess of the pyridine derivative which will be recycled following the reaction, and in a slurry residual from the distillation. The distillate amount is experimentally determined on the basis of distillation curves, by the possibility of almost completely recycling the excess of pyridine compound to the reaction step. Practically, it was found that this amount corresponds to 25–30% of the slurry and that, in this case the total balance of water is correct;

(C) separation by filtering of chromic hydroxide from the filtrate, which is substantially neutral and contains only sodium nicotinate;

(D) recovery of 99.5% pure nicotinic acid from the filtrate according to a known technique, for example consisting of acidification, filtering and extraction with solvent; and (E) recycling of a portion of the produced nicotinic acid corresponding to the required amount for reaction with the pyridine compound in the first stage.

As it results from the above, the amount of oxidant in a lower than stoichiometrical ratio characteristic of the first stage, is equivalent to the excess of reducing agent introduced with the pyridine compound. The reacting pyridine compound may comprise-beta-picoline, gamma-picoline and methylethylpyridine, accordingly a pyridine-3-carboxylic (or nicotinic) acid or a pyridine-4-carboxylic (or isonicotinic) acid, a mixture of nicotinic acid and isocinchomeronic acid (2-5-pyridine-dicarboxylic acid), which is continuously partially recycled, respectively, will be obtained. Where beta-picoline is employed, it may be reacted with sodium bichromate at a temperature in the range of 200°–280° C., at a pressure of between 16 and 45 Kg/sq.cm. for 6–2 hours, and at a pH of between 4.5 and 8.5.

It should be emphasized that the reducing pyridine compound used in excess is recovered by distillation and recycled to the subsequent reactions, and it should be also emphasized that in this operation advantage can be taken of the latent heat of the final reacted mass.

Finally, as to the useful limit of the excess of reducing agent to be used, practically it is to be deduced—which is not to be intended as limitative—that an excess of the reducing agent in a range between 30% and 50% of that foreseen from the stoichiometrical ratio permits recovery by distillation and condensation, in the form of aqueous solution, 90.0% of unreacted reducing agent, this conveniently and without any correction problems.

As further explanation of the present invention, reference should be made to the FIGURE which is a flow sheet illustrating the present process for the preparation of nicotinic acid, particularly sodium nicotinate, from sodium bichromate and beta-picoline.

Some illustrative examples of the present invention follow. These examples are not intended as limitations on the present invention, which is defined by the appended claims.

EXAMPLE 1

An autoclave, maintained under stirring and capable of withstanding an internal pressure up to 100 kg/sq.cm, was charged with 2058 g water, 894 g sodium bichromate crystalized with two molecules of water, 360 g beta-picoline at a titer of 98% and 369 g nicotinic acid at a titer of 99.5%. The resulting pH of the solution in homogeneous phase at 20° C. was 5.6.

The autoclave was heated to an inner mass temperature of 175° C., having a pressure of 10 kg/sq.cm corresponding thereto. The temperature was raised gradually from 175° C. to 250° C. having a pressure of 38 kg/sq.cm corresponding thereto. After 60 minutes, the mass was cooled to room temperature, and, at temperatures lower than 100° C., no further residual pressure was found in the autoclave.

The slurry containing chromic hydroxide thus precipitated was then discharged. The value of this slurry was 7.5. 27.2% by weight of this slurry was then distilled, thus totally recovering the excess of beta-picoline and collecting a condensate of specific gravity substantially close to one, wherein the percentage of beta-picoline was 7.5%. By gas chromatography analysis, only traces of pyridine were found in this aqueous phase, thus showing that no decomposition of nicotinic acid had occurred.

From the slurry, which was a residue from the distillation, chromic hydroxide was removed by filtering, and in the filtrate, which was free of soluble hexavalent chromium, the presence was found by analysis of 860 g of sodium salt of nicotinic acid. After isolation of nicotinic acid, as effected by any of the conventional techniques (such as by acidification, filtering and extraction with solvent), a total weight of 720 g of substantially pure product (titer 99.5%) was obtained, corresponding to a yield of 98.5%. The total yield (including losses during recovery step) corresponds to 95.0%.

369 g of the 720 g of product were recycled for the successive reaction.

EXAMPLE 2

In accordance with Example 1, an autoclave was charged with 258 g water, 894 g sodium bichromate crystalized with two molecules of water, 360 g gamma-picoline having a titer of 99% and 350 g substantially pure isonicotinic acid.

At 20° C., the pH of the resulting solution in homogeneous phase was 5.8.

The heat cycle disclosed in the preceding example was followed to a final temperature of 225° C., at which temperature the corresponding pressure was 25 kg/sq.cm. After 180 minutes of retention at this temperature and this pressure, a mass was cooled and discharged containing precipitated chromic hydroxide. The pH was 8.5. The product was distilled, collecting a condensate of 25% of the mass discharged from the autoclave, in which condensate the presence of 77.9 g γ-picoline was found. Chromatographically, no presence of pyriridine was found in this aqueous phase.

From the residual slurry of the distilling operation, chromic hydroxide was separated by filtering and in the filtrate, in which traces of soluble hexavalent chromium were present, a content of 845 g sodium isonicotinate was analytically found.

From this filtrate, 700 g substantially pure (titer 99.8%) isoconitic acid were recovered.

Yield at the reactor outlet=99.6%
Total yield of the operation=94.6%.

EXAMPLE 3

As in Example 1, an autoclave was charged with 2058 g water, 894 g sodium bichromate crystalized with two molecules water, 160 g methyl-ethyl-pyridine, and 369 g nicotinic acid having a titer of 99.5%. The solution was homogeneous above 45° C. and at 50° C. the pH value was 4.5.

The heat cycle as described in the preceding example was followed, according to the operative modalities also described therein.

After 90 minutes of retention at 225° C., the residual mass containing precipitated chromic hydroxide was cooled and discharged; the pH value was 8.3.

By means of the distillation the unreacted organic phase was recovered, collecting a condensate, wherein in the ratios as shown in parenthesis, methyl-ethyl-pyridine (75%), ethyl-pyridine (15%), and pyridine (10%) were present together with water. The presence of ethyl-pyridine indicated a partial oxidation and the presence of pyridine indicated decomposition by total decarboxylation of isocinochomeric acid.

Chromic hydroxide was separated by filtration in the distillation residue. In the aqueous phase of the filtrate thus obtained, not very high yield values for the acid were found upon analysis, corresponding to values not exceeding 50%. In fact the total presence of nicotinic acid used in the autoclave charging was found, plus an amount of mixture of isocinchomeric acid (12%) and nicotinic acid (88%), so that as calculated on the reacted methyl-ethyl pyridine, the yield did not exceed 50%.

EXAMPLE 4

An industrial type of autoclave was charged with 1340 kg aqueous solution of sodium bichromate, containing 546.7 kg $Na_2Cr_2O_7.2H_2O$ and 793.3 kg water; 597 kg aqueous solution of beta-picoline, recovered by distillation from preceding reactions and containing 100% beta-picoline in an amount of 52.2 kg; 170 Kg beta-picoline having a titer of 98%; and 225 kg nicotinic acid having a titer of 98.4%.

The resulting homogeneous solution, having a specific gravity of 1.23 g/cu cm and pH, measured at 20° C., of 5.8 was heated to 235° C. for one hour at a corresponding pressure of 35 kg/sq.cm. This temperature was maintained for 2 hours.

An automatic control system permitted following a predetermined linear heat profile in temperature-time diagram, both during heating and reaction. This was achieved by introducing and circulating high pressure steam as a heating agent, and water as a cooling agent. A reaction completion, 800 kg aqueous solution containing 100% beta-picoline in an amount of 58.1 kg were distilled and collected by condensation.

The mass from the autoclave was discharged at about 100° C., such a mass still containing about 0.9 kg beta-picolina.

The chromic hydroxide was filtered and a solution of sodium nicotinate containing 858.5 kg of this salt, as analytically determined was recovered.

By known techniques, 425 kg nicotinic acid having a titer of 99.5% were recovered from the solution. Of these 425 kg, a portion of 202.5 kg was discharged as final product, and the remainder was recycled to the successive operation.

Yield at the reaction end=99.2%.
Total operation yield=94.8%.
Consumption of 98% beta-picoline per kg of 99.5% produced nicotinic acid=0.81.

What is claimed is:

1. An oxidation process for preparing pyridin-carboxylic acid from alkyl pyridine compounds comprising the steps of:
   (A) reacting
      (1) a hydrosoluble hexavalent chromium oxidizing compound, with
      (2) an alkyl pyridine compound, nucleus substituted by alkyl groups oxidizable to carboxylic groups, connected through a carbon-to-carbon bond, and present in an amount from 30 to 50 percent in excess of the stoichiometric ratio for an reduction reaction,
   in the presence of carboxylic acid of the same type as that released in the oxidation reaction and in the same amount as the latter; said reaction being carried out in homogeneous phase in the presence of not less than 40 moles of water per mole of carboxylic acid, at a temperature of from 150° to 300° C., at a pH of from 4.5 to 8.5, at a pressure corresponding to the vapor pressure of the reaction mixture at such a temperature, and for the time required for a complete oxidation from the hexavalent to a trivalent chromium compound under the above conditions, to form a reaction slurry;
   (B) distilling the reaction slurry to separate a condensate having a specific gravity of about one, containing the excess of the alkyl pyridine compound relative to the stoichiometric amount, with a remaining residual slurry;
   (C) filtering the remaining residual slurry to separate produced chromic hydroxide and a substantially neutral aqueous solution of the sodium salt of the desired pyridincarboxylic acid as a single solute;
   (D) recovering pyridin-carboxylic acid of at least 99.5% purity by acidification, filtration and extraction;
   (E) recycling such portion of the product thus obtained as the carboxylic acid of step (A) as is required; and
   (F) recycling the excess alkyl pyridine compound to step (A).

2. The process of claim 1 wherein the alkyl pyridine compound is beta-picoline, gamma-picoline or methyl ethyl pyridine.

3. The process of claim 1 wherein the hydrosoluble hexavalent chromium oxidizing compound is an alkaline bichromate.

4. The process of claim 3 wherein the alkaline bichromate is sodium bichromate.

5. The process of claims 1, 2, 3 or 4 wherein step (A) is conducted at a temperature of from 175° to 250° C.

6. The process of claims 1, 2, 3 or 4 wherein step (A) is conducted at a pH of from 5.5 to 8.0.

7. The process of claims 1, 2, 3 or 4 wherein step (A) is conducted for a time of from 1 to 8 hours.

8. The process of claims 1, 2, 3 or 4 wherein step (A) is conducted at a temperature of from 175° to 250° C., at a pH of from 5.5 to 8.0, and for a time of from 1 to 8 hours.

9. The process of claim 8 wherein step (A) is conducted at a temperature of at least 200° C. for a time of from 2 to 6 hours.

10. The process of claim 9 wherein step (A) is conducted for a time not exceeding 4 hours.

11. The process of claim 10 wherein step (A) is conducted at a temperature of from 225° to 250° C. for a time of from 1 to 3 hours.

12. The process of claim 11 wherein step (A) is a reaction between sodium bichromate and beta-picoline in the presence of nicotinic acid, conducted at a homogeneous phase pH of about 5.6, at a temperature of about 250° C. and for about 3 hours.

13. The process of claim 11 wherein step (A) is a reaction between sodium bichromate and gamma-picoline in the presence of isonicotinic acid, conducted at a homogeneous phase pH of about 5.8, at a temperature of about 225° C. and for about 3 hours.

14. The process of claim 11 wherein step (A) is a reaction between sodium bichromate and methyl ethyl picoline in the presence of nicotinic acid, conducted at a homogeneous phase pH of about 4.5, at a temperature of about 225° C. and for about 90 minutes.

15. The process of claim 11 wherein step (A) is a reaction between sodium bichromate and beta-picoline in the presence of nicotinic acid, conducted at a homogeneous phase pH of about 5.8, at a temperature of about 235° C. and for about 3 hours.

16. The process of claims 1, 2, 3 or 4 wherein step (A) is conducted at a vapor pressure of between 16 and 45 kg/cm$^2$ for a period of from 2 to 6 hours and at a homogeneous phase pH of between 5.5 and 8.

* * * * *

UNITED STATES PATENT AND TRADEMARK OFFICE
CERTIFICATE OF CORRECTION

PATENT NO. : 4,217,457
DATED : August 12, 1980
INVENTOR(S) : Giovanni Ghelli

It is certified that error appears in the above—identified patent and that said Letters Patent is hereby corrected as shown below:

Column 1, line 37, delete "described" and substitute --cited--.

Signed and Sealed this

Fifteenth Day of December 1981

[SEAL]

Attest:

*Attesting Officer*

GERALD J. MOSSINGHOFF

*Commissioner of Patents and Trademarks*